United States Patent [19]

Carter et al.

[11] Patent Number: 5,286,745
[45] Date of Patent: Feb. 15, 1994

US005286745A

[54] ANTIBIOTICS LL-E19020 EPSILON AND LL-E19020 EPSILON$_1$

[75] Inventors: Guy T. Carter, Suffern; Joseph J. Goodman, Spring Valley, both of N.Y.

[73] Assignee: American Cyanamid Company, Wayne, N.J.

[21] Appl. No.: 756,931

[22] Filed: Sep. 9, 1991

[51] Int. Cl.$^5$ ............... A61K 31/35; C07D 315/00
[52] U.S. Cl. ........................... 514/459; 549/414
[58] Field of Search ........... 549/496, 414; 514/471, 514/459

[56] References Cited

U.S. PATENT DOCUMENTS

| | | | |
|---|---|---|---|
| 4,704,276 | 11/1987 | Kantor | 424/122 |
| 4,705,688 | 11/1987 | Carter et al. | 424/122 |
| 4,968,493 | 11/1990 | Carter et al. | 424/122 |

FOREIGN PATENT DOCUMENTS 442783  8/1991  European Pat. Off. .

OTHER PUBLICATIONS

Journal of Antibiotics, 41 (10), 1511–1514 Oct. 1988.
Journal of Chromatography, 484, 381–390 (1989).
Journal of Antibiotics, 41(10), 1293–1299 Oct. 1988.
Journal of Antibiotics, 41(10), 1300–1315 Oct. 1988.
Journal of Antibiotics, 39(10), 1361–1367 Oct. 1986.
Journal of Antibiotics, 42(1), 94–101 Jan. 1989.
Antimicrobial Agents and Chemotherapy, 33 (3), 322–325 Mar. 1989.
Program and Abstracts of the 27th Interscience Conference on Antimicrobial Agents and Chemotherapy, No. 995, p. 270, New York, Oct. 4–7 1987.

*Primary Examiner*—C. Warren Ivy
*Assistant Examiner*—A. Owens
*Attorney, Agent, or Firm*—T. S. Szatkowski

[57] ABSTRACT

The invention provides antibiotics designated LL-E19020 Epsilon and LL-E19020 Epsilon$_1$ which are derived from the microorganism *Streptomyces lydicus* ssp. *tanzanius* NRRL 18036.

4 Claims, 8 Drawing Sheets

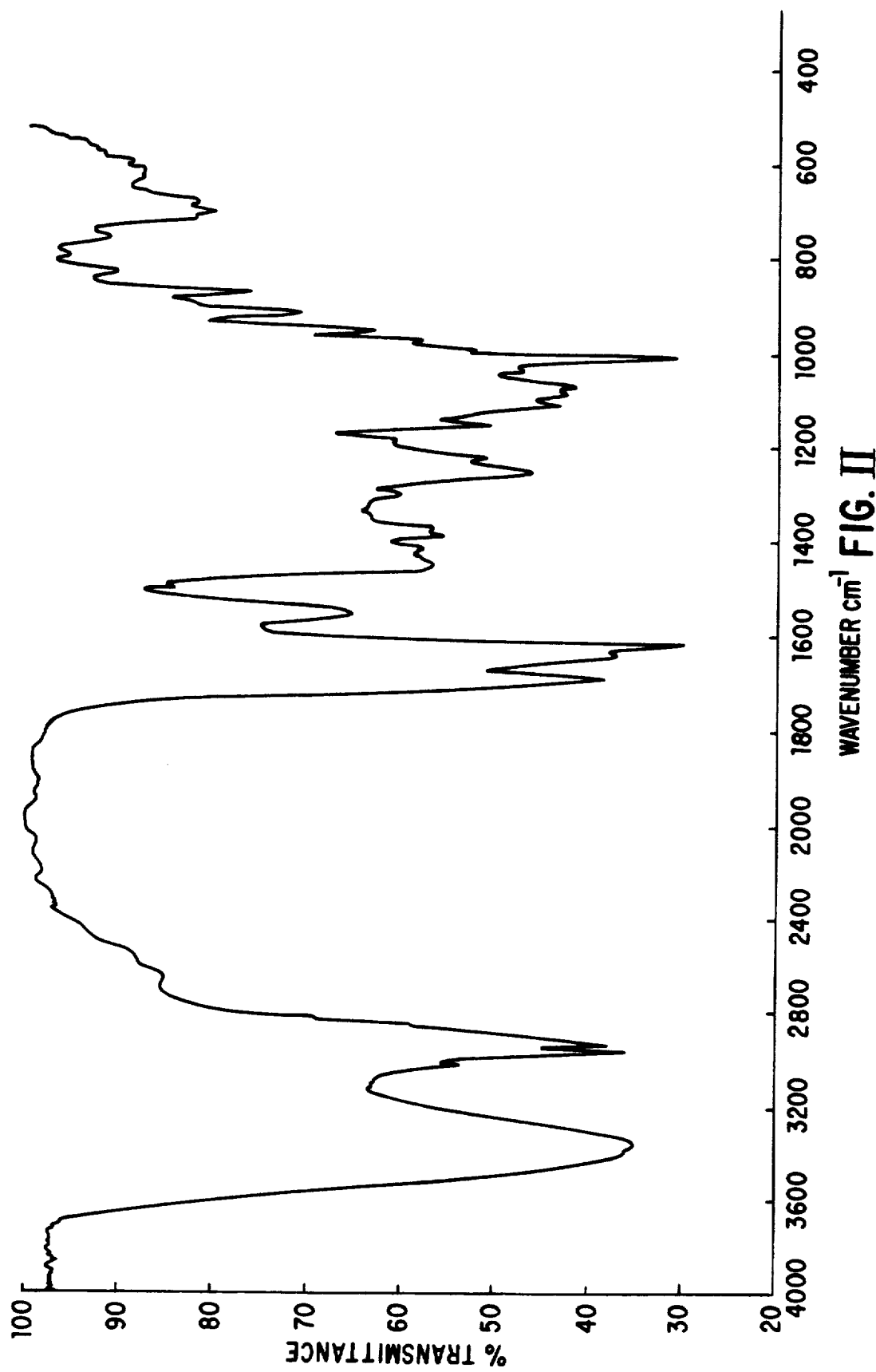
FIG. II

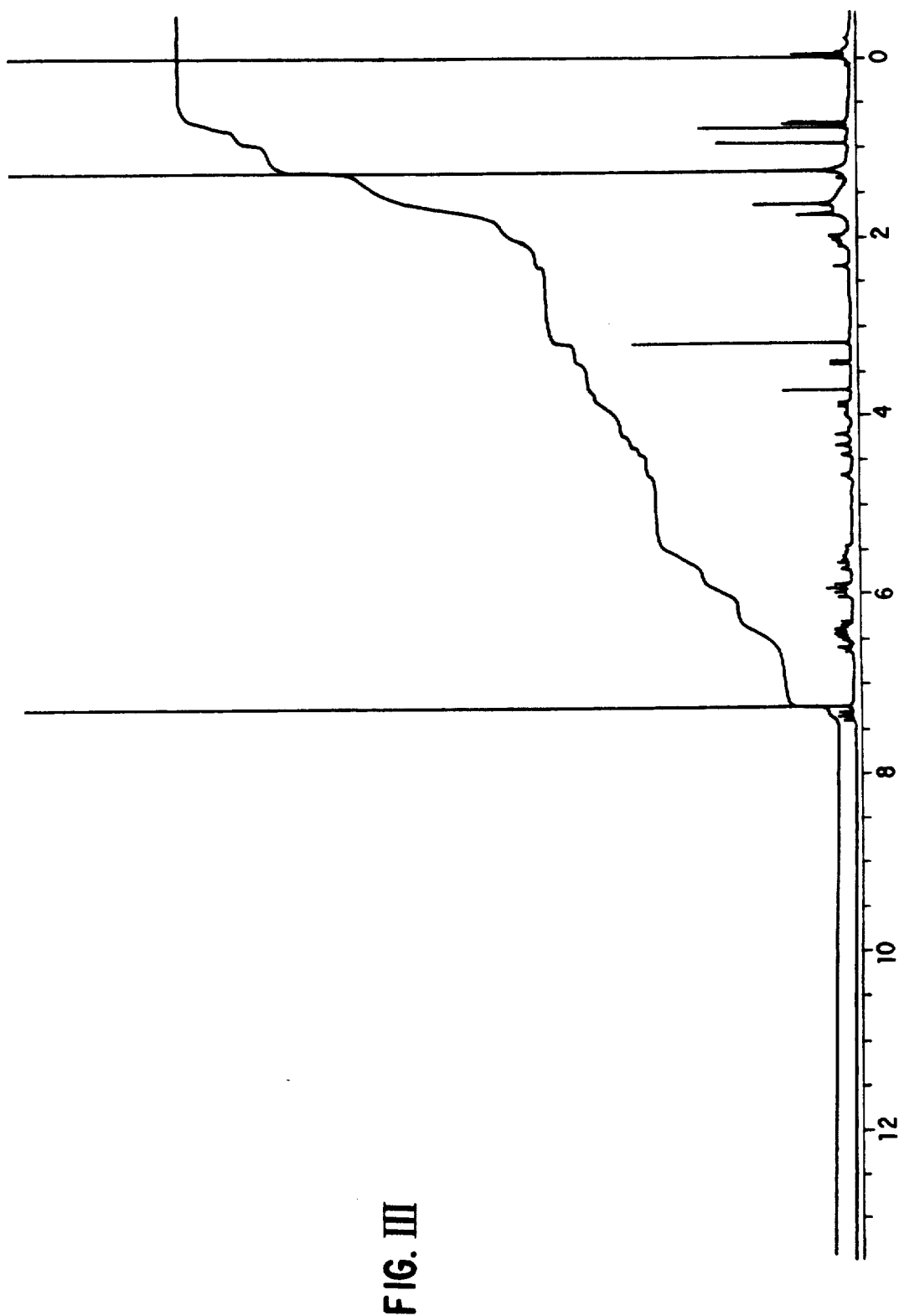
FIG. III

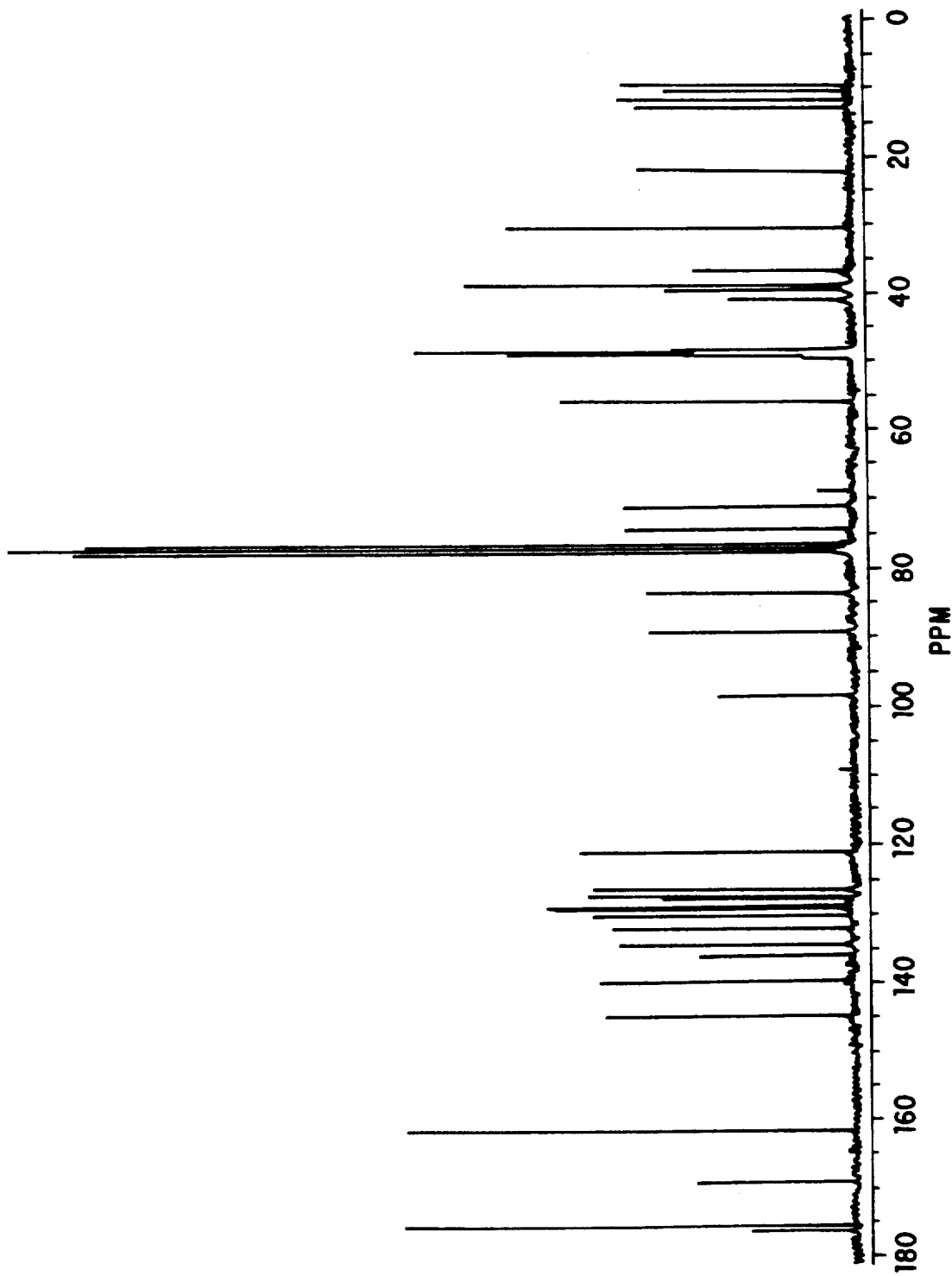
FIG. IV

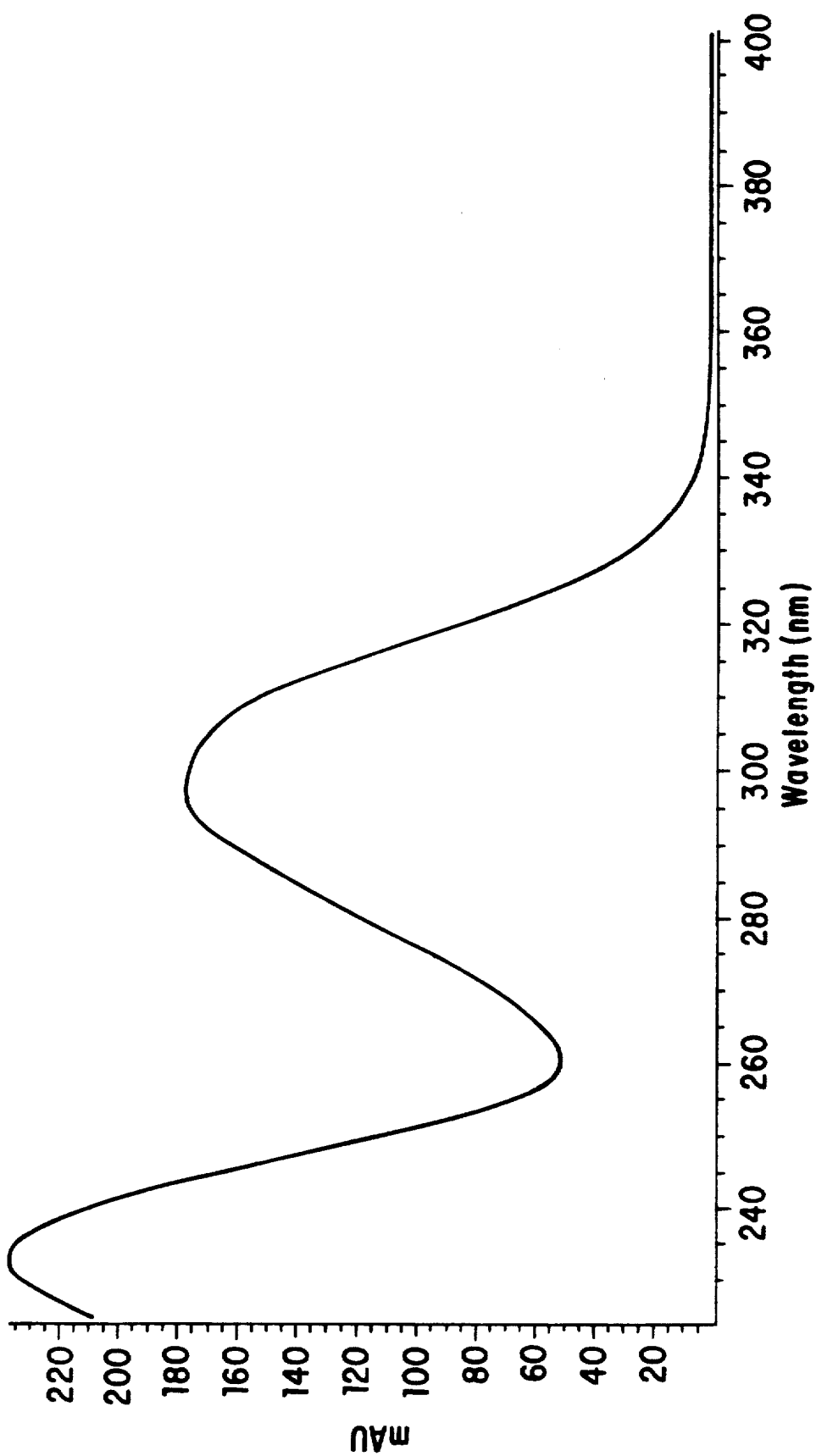
FIG. V

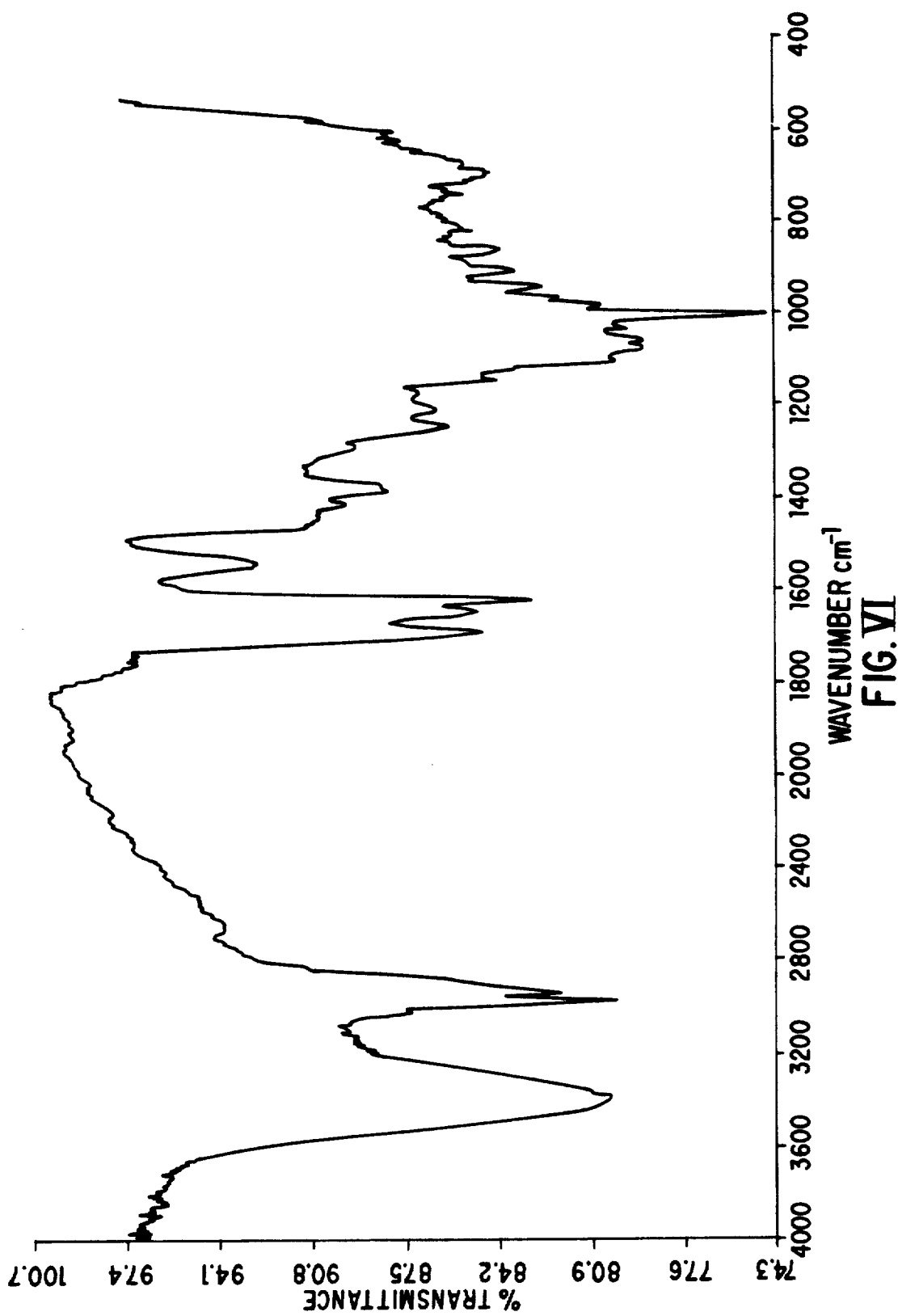
FIG. VI

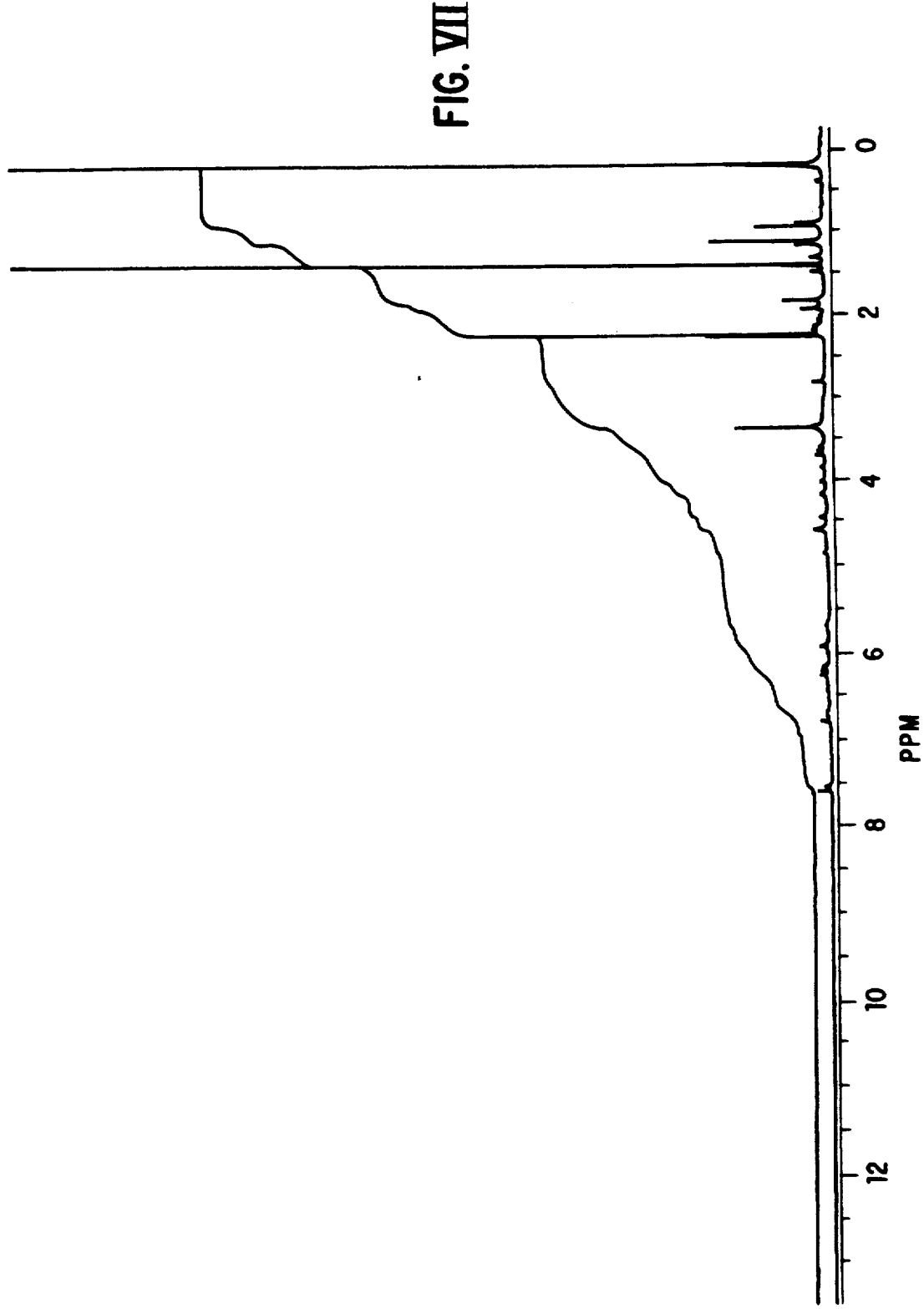
FIG. VII

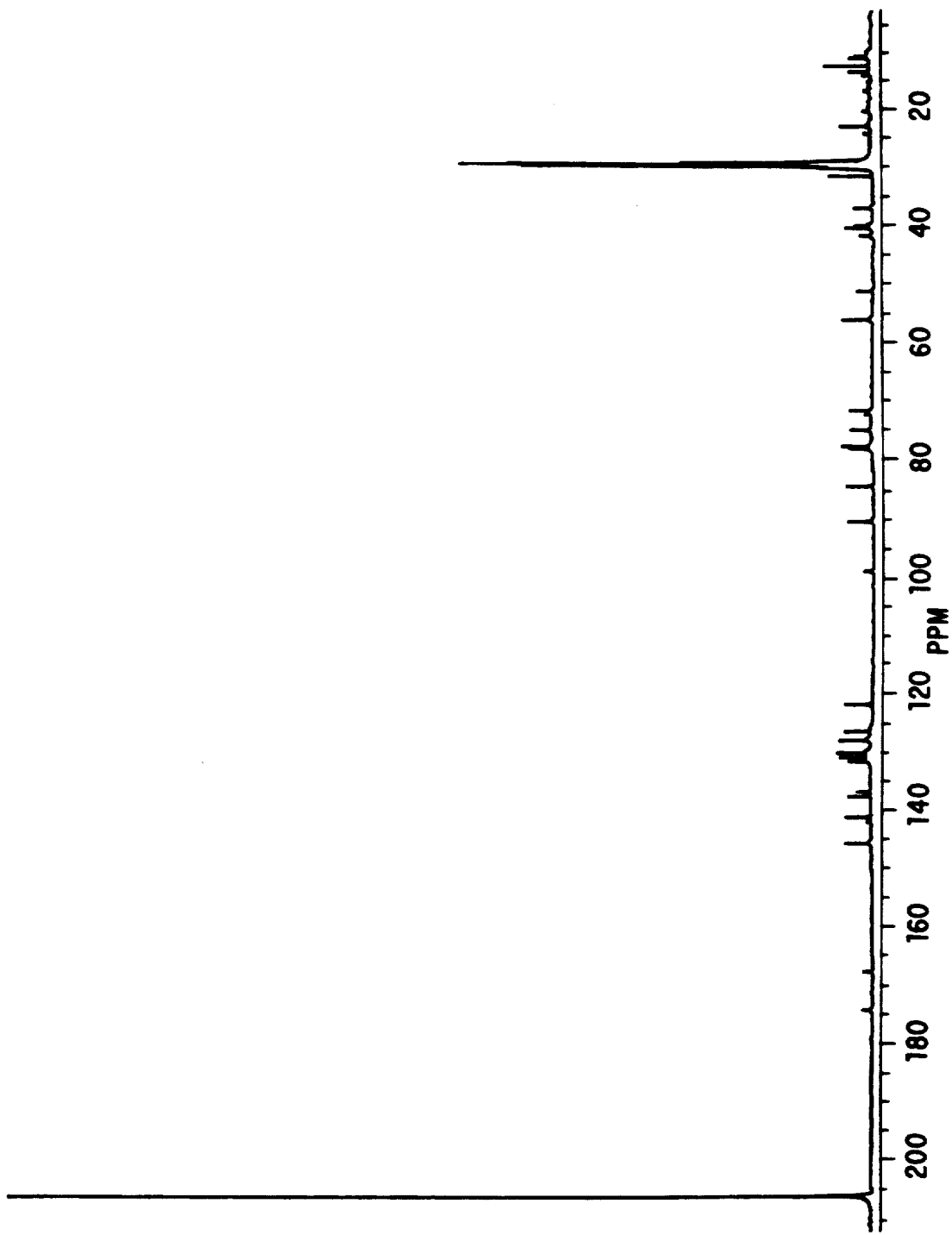
FIG. VIII

ANTIBIOTICS LL-E19020 EPSILON AND LL-E19020 EPSILON$_1$

BACKGROUND OF THE INVENTION

1. Field of the Invention

The invention relates to new antibiotics designated LL-E19020 Epsilon and LL-E19020 Epsilon$_1$, to their production by fermentation and to a process for their recovery and purification.

2. Description of the Prior Art

Antibiotics LL-E19020 Alpha and LL-E19020 Beta are disclosed in U.S. Pat. No. 4,705,688, The Journal Of Antibiotics, 41(10), 1511-1514 (1988) and The Journal Of Antibiotics, 42(10), 1489-1493 (1989). Antibiotic LL-E19020 Alpha has a trisaccharide attached at C-21a, a phenylacetate ester group attached at C-23 and has the structure:

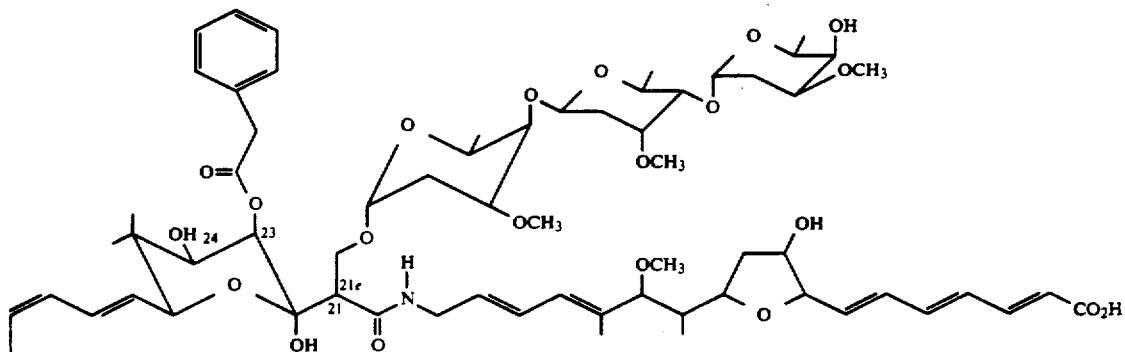

Antibiotic LL-E19020 Beta has a trisaccharide attached at C-21a, a phenylacetate ester group attached at C-24 and has the structure:

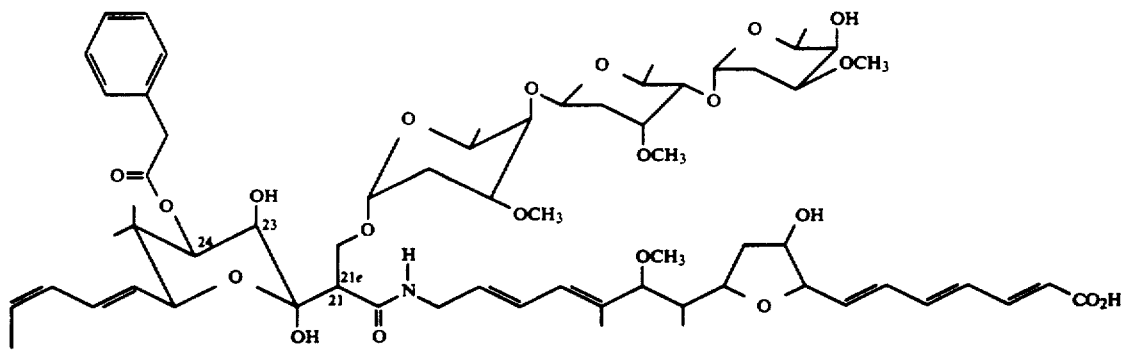

A process for purification of the antibiotic LL-E19020 Alpha by reversed phase HPLC purification is described in J. of Chrom. 484, 381-390(1989). Antibiotics LL-E19020 Alpha and LL-E19020 Beta are also useful for increasing the growth rate of meat producing animals and for treating respiratory disease, fowl cholera and necrotic enteritis as described in U.S. Pat. No. 4,704,276 and U.S. Pat. No. 4,968,493.

A related family of compounds, the phenelfamycins, is reported in The Journal Of Antibiotics, 41(10), 1293-1299 (1988); The Journal Of Antibiotics, 41(10), 1300-1315 (1988); The Journal Of Antibiotics, 39(10), 1361-1367 (1986); The Journal Of Antibiotics, 42(1), 94-101 (1989); Antimicrobial Agents and Chemotherapy, 33(3), 322-325 (1989); Program and Abstracts Of The 27th Interscience Conference on Antimicrobial Agents Chemotherapy, No. 995, p 270, New York, Oct. 4-7 1987.

SUMMARY OF THE INVENTION

New antibiotics designated LL-E19020 Epsilon and LL-E19020 Epsilon$_1$ have now been found. The structure of the new antibiotic LL-E19020 Epsilon is:

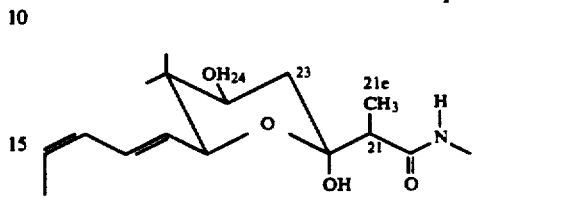

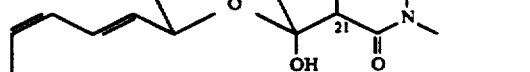

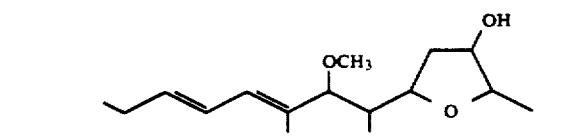

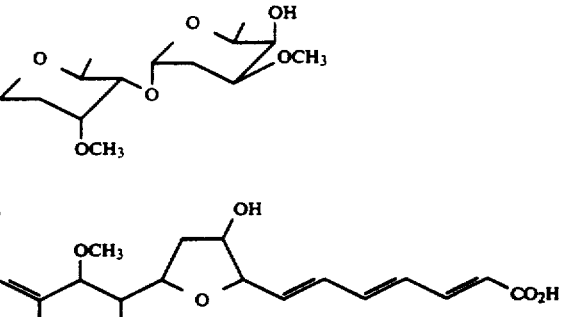

As can be determined from the above structure, antibiotic LL-E19020 Epsilon differs from the previously known antibiotics LL-E19020 Alpha and LL-E19020 Beta in that LL-E19020 Epsilon lacks the trisaccharide attached at C-21a and lacks the phenyl acetate ester group attached at C-23 or C-24. In addition C-23 is reduced to a methylene. The physico chemical characteristics of LL-E19020 Epsilon are as follows:

1. Molecular weight: 643 (FABMS=M/Z 666 corresponding to [M+Na]+)
2. Molecular formula: $C_{36}H_{53}NO_9$
3. Specific optical rotation: $[\alpha]_{D} = +24^{\circ 26}(1.53, MeOH)$
4. Ultraviolet Absorption Spectrum as shown in FIG. 1.
   UV absorption [MeOH]λmax (ε): 232 nm (52,000); 290 nm (38,000).
5. IR absorption spectrum as shown in FIG. II.
   IR absorption spectrum $[KBr]\nu_{max}$: 3384, 2973, 2935, 1690, 1639, 1619, 1548, 1451, 1385, 1298, 1151, 1007 cm$^{-1}$:
6. Proton $^1$H NMR[CDCl$_3$]: Spectrum (300 MHz) as shown in FIG. III.
7. Carbon 13 $^{13}$C NMR[CDCl$_3$]Spectrum as shown in FIG. IV, significant peaks listed below (δ from TMS): 176.1, 170.5, 146.1, 140.4, 136.7, 134.4, 132.1, 130.2, 129.1, 128.8, 128.6, 128.5, 128.2, 127.4, 126.1, 120.5, 98.43, 89.20, 83.18, 77.71, 76.69, 74.70, 72.05, 56.06, 49.06, 41.43, 39.84, 39.21, 39.12, 37.42, 22.42, 13.48, 13.12, 11.87, 10.75, 10.05.
8. High pressure liquid chromatography (HPLC) retention time of 12.6 minutes using a gradient of acetonitrile in aqueous acetic acid.
9. High pressure liquid chromatography (HPLC) retention time of 11.4 minutes using a gradient of dioxane in aqueous acetic acid.

The structure of the new antibiotic LL-E19020 Epsilon$_1$ is identical to that of LL-E19020 Epsilon except that LL-E19020 Epsilon$_1$ is the C-21 epimer of LL-E19020 Epsilon. The physico chemical characteristics of LL-E19020 Epsilon$_1$ are as follows:

1. Molecular weight: 643
   (Thermospray=M/Z 643 for M$^-$)
2. Molecular formula: $C_{36}H_{53}NO_9$
3. Ultraviolet Absorption Spectrum as shown in FIG. V.
   UV absorption [MeOH]$\nu_{max}$: 232 nm; 290 nm.
4. IR absorption spectrum as shown in FIG. VI.
   IR absorption spectrum [KBr] $\nu_{max}$: 3400, 2973, 1690, 1642, 1618, 1248, 1178, 1149, 1083, 1007 cm$^{-1}$.
5. Proton $^1$H NMR[CDCl$_3$]: Spectrum (300 MHz) as shown in FIG. VII.
6. Carbon 13 $^{13}$C NMR[CDCl$_3$] Spectrum as shown in FIG. VII, significant peaks listed below (δ from TMS): 176.1, 170.5, 146.0, 140.4, 136.6, 134.4, 132.1, 130.1, 129.1, 128.8, 128.5, 128.5, 128.5, 127.4, 126.0, 120.6, 98.44, 89.23, 83.20, 77.71, 77.20, 74.69, 72.03, 56.04, 49.07, 41.43, 39.86, 39.22, 39.11, 37.41, 22.42, 13.45, 13.14, 11.88, 10.76, 10.06.
7. High pressure liquid chromatography (HPLC) retention time of 9.9 minutes using a gradient of acetonitrile in aqueous acetic acid.
8. High pressure liquid chromatography (HPLC) retention time of 9.4 minutes using a gradient of dioxane in aqueous acetic acid.

The new antibiotics LL-E19020 Epsilon and LL-E19020 Epsilon$_1$ are formed along with LL-E19020 Alpha and LL-E19020 Beta during cultivation under controlled conditions of a strain of *Streptomyces lydicus* ssp. *tanzanius*, NRRL 18036. The new antibiotics LL-E19020 Epsilon and LL-E19020 Epsilon$_1$ are separated from LL-E19020 Alpha and LL-E19020 Beta and subsequently purified by high pressure liquid chromotography (HPLC).

BRIEF DESCRIPTION OF THE DRAWINGS

FIG. I shows the ultraviolet absorption spectrum of LL-E19020 Epsilon.

FIG. II shows the infrared absorption spectrum of LL-E19020 Epsilon.

Figure 1:
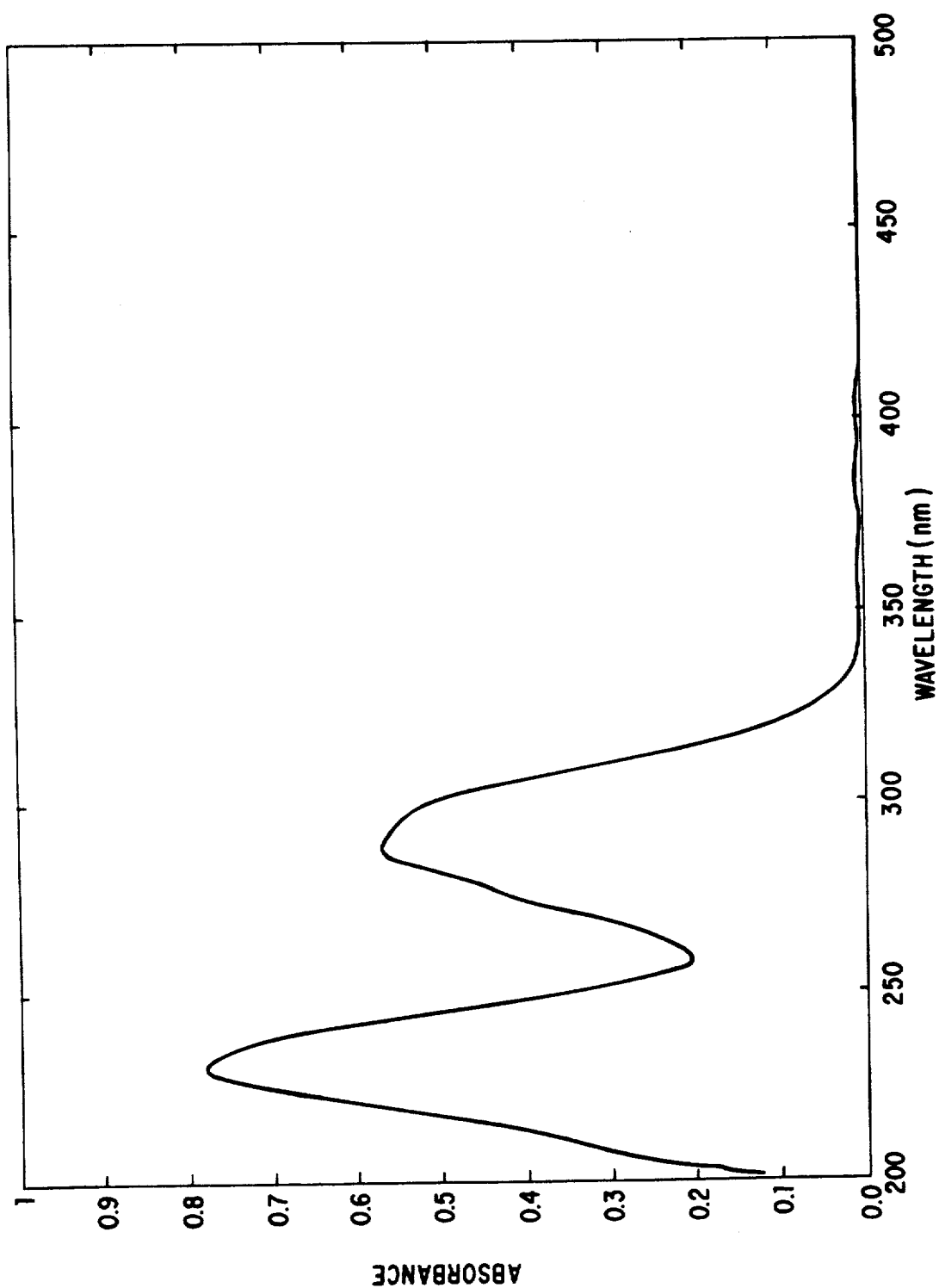

FIG. III shows the proton nuclear magnetic resonance spectrum of LL-E19020 Epsilon.

FIG. IV shows the carbon-13 nuclear magnetic resonance spectrum of LL-E19020 Epsilon.

FIG. V shows the ultraviolet absorption spectrum of LL-E19020 Epsilon$_1$.

FIG. VI shows the infrared absorption spectrum of LL-E19020 Epsilon$_1$.

FIG. VII shows the proton nuclear magnetic resonance spectrum of LL-E19020 Epsilon$_1$.

FIG. VIII shows the carbon-13 nuclear magnetic resonance spectrum of LL-E19020 Epsilon$_1$.

DESCRIPTION OF THE PREFERRED EMBODIMENTS

The antibiotics LL-E19020 Epsilon and Epsilon$_1$ are produced by fermentation of a strain of *Streptomyces lydicus*, ssp. *tanzanius*, NRRL 18036, in an aqueous nutrient medium containing assimilable sources of carbon and nitrogen under submerged aerobic conditions. This microorganism is maintained in the culture collection of the Medical Research Division, American Cyanamid Company, Pearl River, N.Y. as culture number LL-E19020. A viable culture of this new microorganism has been deposited with the Patent Culture Collection Laboratory, Northern Regional Research Center, U.S. Department of Agriculture, Peoria, Ill. 61604, and has been added to its permanent collection. It has been assigned the strain designation NRRL 18036 by said depository.

Culture LL-E19020 produces short spiral spore chains, 10–50 spores long, with occasional longer chains. These tend to coalesce to form dry blackish masses on such ISP media as oatmeal and inorganic salts-starch. The spores have smooth surfaces as assessed by electron microscopy. The strain contains the L isomer of diaminopimelic acid, and may thus be assigned to the genus Streptomyces.

In the ISP tests for utilization of carbohydrates, LL-E19020 shows growth on arabinose, fructose, inositol, mannitol, reffinose, rhamnose, sucrose and xylose. Cellulose is not utilized.

The reactions of LL-E19020 in the Gordon physiological series are compared in the following Table I with those of *Streptomyces lydicus* ISP 5461 which it most closely resembles morphologically and physiologically.

Because LL-E19020 differs from ISP 5461 in five(5) characteristics (xanthine hydrolysis, decarboxylation of oxalate, acid from erythritol, rhamnose and β-methyl-D-xyloside) it is designated as a subspecies of *Streptomyces lydicus*.

TABLE I

| Gordon Test Reactions Of LL-E19020 And *Streptomyces lydicus* ISP 5461 | | |
|---|---|---|
| Reactions | LL-E19020 | ISP 5461 |
| Degradation/Transformation of | | |
| Casin | + | + |
| Xanthine | − | + |
| Hypoxanthine | + | + |
| Tyrosine | + | + |
| Adenine | + | + |

TABLE I-continued

Gordon Test Reactions Of LL-E19020
And *Streptomyces lydicus* ISP 5461

| Reactions | LL-E19020 | ISP 5461 |
|---|---|---|
| Production of | | |
| Amylase | + | + |
| Gelatinase | + | + |
| Phosphatase | + | + |
| Nitrate Reductase | − | − |
| Urease | + | + |
| Esculinase | + | + |
| Growth on/in | | |
| 5% Sodium chloride | + | + |
| Salicylate | − | − |
| Lysozyme Broth | trace | trace |
| Utilization of | | |
| Acetate | + | + |
| Benzoate | + | + |
| Citrate | + | + |
| Lactate | + | + |
| Malate | + | + |
| Mucate | + | + |
| Oxalate | + | − |
| Propionate | + | + |
| Pyruvate | + | + |
| Succinate | + | + |
| Tartrate | − | − |
| Growth at | | |
| 10° C. | + | + |
| 42° C. | − | − |
| 50° C. | − | − |
| Acid from | | |
| Adonitol | + | + |
| Arbinose | + | + |
| Cellobiose | + | + |
| Dextrin | + | + |
| Dulcitol | − | − |
| Erythritol | + | − |
| Fructose | + | + |
| Galactose | + | + |
| Glucose | + | + |
| Glycerol | + | + |
| Inositol | + | + |
| Lactose | + | + |
| Maltose | + | + |
| Mannitol | + | + |
| Mannose | + | + |
| Melibiose | + | + |
| α-Methyl-D-Glucoside | + | + |
| Raffinose | + | + |
| Rhamnose | + | − |
| Salicin | + | + |
| Sobitol | + | + |
| Sucrose | + | + |
| Trehalose | + | + |
| Xylose | + | + |
| β-Methyl-D-Xyloside | + | − |

It is to be understood that for the production of these new antibacterial agents the present invention is not limited to this particular organism or to organisms fully answering the above characteristics which are given for illustrative purposes only. In fact, it is desired and intended to include the use of mutants produced from this organism by various means such as exposure of X-radiation, ultraviolet radiation, N'-methyl-N'-nitro-N-nitrosoguanidine, actinophages and the like.

Cultivation of *Streptomyces lydicus* ssp. *tanzanius* NRRL 18036 may be carried out in a wide variety of liquid culture media. Media which are useful for the production of LL-E19020 Epsilon and LL-E19020 Epsilon₁ include an assimilable source of carbon, such as dextrin, sucrose, molasses, glycerol, etc; an assimilable source of nitrogen such as protein, protein hydrolysate, polypeptides, amino acids, corn steep liquor, etc; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

The antibiotics LL-E19020 Epsilon and LL-E19020 Epsilon₁ are recovered from the fermentation broth by extraction of the broth.

EXAMPLE 1

Inoculum Preparation

A typical medium used to grow the primary inoculum is prepared according to the following formula:

| | |
|---|---|
| Dextrose | 1.0% |
| Dextrin | 2.0% |
| Yeast extract | 0.5% |
| NZ Amine A | 0.5% |
| Calcium carbonate | 0.1% |
| Water qs | 100.0% |

NOTE:
NA Amine A is a pancreatic digest of casein, registered trademark of Scheffield Chemical, Norwich, New York.

This medium is sterilized and 100 ml, in a 500 ml flask, is inoculated with *Streptomyces lydicus* ssp. *tanzanius* NRRL 18036. The medium is then placed on a rotary shaker and incubated at 28° C. for 48 hours providing a primary inoculum. This primary inoculum is then used to inoculate 10 liters of the same sterile medium in a bottle except that 0.3% v/v silicone antifoam is also added. This culture is grown for 48 hours providing a secondary inoculum. This secondary inoculum is then used to inoculate 300 liters of the same sterile medium in a fermenter.

EXAMPLE 2

Fermentation

A fermentation production of the following formulation is prepared:

| | |
|---|---|
| Dextrin | 7.0% |
| Dextrose | 0.5% |
| Soy flour | 1.5% |
| Corn steep liquor | 0.5% |
| Calcium carbonate | 0.5% |
| Silicone antifoam | 0.3% |
| Water qs | 100.0% |

This medium is sterilized and is then inoculated with 10 liters of secondary inoculum from Example 1 to a final volume of 300 liters. The fermentation is conducted at 30° C. with a sterile air flow of 0.67 liters of air per liter of mash per minute and agitation by an impeller driven at 200 rpm for 92-93 hours, at which time the mash is harvested.

EXAMPLE 3

Isolation and Purification of LL-E19020 Epsilon and LL-E19020 Epsilon₁

The harvest mash from two (2) fermentations conducted as described in Example 2 making a total volume of 503 liters is diluted with 6 liters of toluene. The pH is adjusted to 4.5 using concentrated hydrochloric acid. While stirring, 250 liters of methyl alcohol is added.

Stirring is continued over 2 hours and the pH is continuously monitored. To the mixture is added 50 pounds of diatomaceous earth followed by stirring for 15 minutes. The mixture is filtered through a filter press with the press washed with 75 liters of water. The total volume collected is 697 liters. A 45 liter HP-20 column is prepared by washing the resin with 100 liters of deionized water at a rate of 1 to 2 liters/minute followed by 120 liters of 1:1 1N sodium hydroxide/methyl alcohol at a rate of 1 to 2 liters/minute followed by 100 liters of deionized water at a rate of 1 to 2 liters/minute followed by 120 liters of 1N sulfuric acid at a rate of 1 to 2 liters/minute followed by 100 liters of deionized water at a rate of 1 to 2 liters/minute. The pH of the eluate is checked and additional deionized water wash could be needed to bring the pH to between 6 and 7. The column is further washed with 100 liters of methyl alcohol at a rate of 1 to 2 liters/minute followed by 100 liters of deionized water. The column is further washed at a rate of 1 to 2 liters/minute with a solution of 108 liters of acetone and 12 liters of water followed by 100 liters of acetone at a rate of 1 to 2 liters/minute and concluded with 100 liters of deionized water at a rate of 1 to 2 liters/minute. The 697 liters of liquid from the filter press is added to the prepared HP-20 column at a rate of 1 liter/minute. The column is further washed with 120 liters of deionized water at a rate of 1 liter/minute followed by a solution of 64 liters of deionized water and 16 liters of acetone at a rate of 1 liter/minute. Four 20 liter fractions are collected and designated F1-F4. The column is further washed with a solution made from 48 liters of deionized water and 32 liters of acetone at a rate of 0.5 to 1 liter/minute to afford four 20 liter fractions which are collected and labeled F5-F8. Further washing of the column with a solution made from 32 liters of deionized water and 48 liters of acetone at a rate of 0.5 to 1 liter/minute affords four 20 liter collected fractions designated F9-F12. The column is further washed with a solution made from 16 liters of water and 64 liters of acetone at a rate of 0.5 to 1 liter/minute to afford four 20 liter collected fractions designated as F13-F16. Further washing of the column with acetone at a rate of 0.5 to 1 liter/minute affords four 20 liter collected fractions designated F17-F20. Fraction 16 is concentrated and freeze dried to afford 36.8 g of material which is purified by high pressure liquid chromatography (HPLC) on a $C_{18}$ reverse phase column (5.0×25 cm) by elution with 50-52% dioxane in 1% aqueous acetic acid. Thirteen fractions are collected. Fraction 5 is evaporated to afford 121 mg of LL-E19020 Epsilon. Fraction 2 is further purified by high pressure liquid chromatography on a $C_{18}$ reverse phase column (5.0×25 cm) by elution with 30% acetonitrile in 1% acetic acid to afford 19.5 mg of LL-E19020 Epsilon$_1$.

Analytical High Pressure Liquid Chromatography (HPLC)

The LL-E19020 Epsilon and Epsilon$_1$ components are analyzed using two different analytical HPLC systems. Their retention time compared to LL-E19020 $\alpha$ and $\beta$ are indicated in the table below.

| COMPONENTS | RETENTION TIME (MINUTES) | |
|---|---|---|
| | SYSTEM A | SYSTEM B |
| LL-E19020 Alpha | 22.7 | 23.5 |
| LL-E19020 Beta | 27.6 | 26.7 |
| LL-E19020 Epsilon | 12.6 | 11.4 |
| LL-E19020 Epsilon$_1$ | 9.9 | 9.4 |

A. HPLC system: Alltech adsorbosphere HS 5$\mu$ C18 column (4.6×250 mm) with guard column, eluted with a gradient of acetonitrile in 1% aqueous acetic acid. The starting composition is 40% acetonitrile linearly increasing to 70% over 25 minutes and holding at 70% for 5 minutes. The flow rate is 1.0 mL per minute.

B. HPLC system: Alltech adsorbosphere HS 5$\mu$ C18 (4.6×250 mm) with guard column, eluted with a gradient of dioxane in 1% aqueous acetic acid. The starting composition is 55% dioxane, increasing to 70% over 25 minutes and holding at 70% for 5 minutes. The flow rate is 1.0 mL per minutes.

EXAMPLE 4

In Vitro Antibacterial Activity of LL-E19020 Epsilon and LL-E19020 Epsilon$_1$

The in vitro antibacterial activity of LL-E19020 Epsilon and LL-E19020 Epsilon$_1$ is determined against a spectrum of gram positive and gram negative bacteria by a standard agar dilution method. Mueller-Hinton agar containing 5% sheep blood and two-fold decreasing concentrations of LL-E19020 Epsilon and LL-E19020 Epsilon$_1$ are poured into petri dishes. The agar surfaces were inoculated with 1 to $5 \times 10^4$ colony forming units of bacteria by means of the Steers replicating device. The lowest concentration of antibiotic that inhibits growth of a bacterial strain after 18 hours incubation is recorded as the minimal inhibitory concentration for that strain.

Minimum Inhibitory Concentration Procedure By Agar Dilution

1. Serial two-flow dilutions of drug are prepared in Mueller-Hinton broth in a range of 2560 $\mu$g/ml–0.15 $\mu$g/ml plus a solvent control.
2. Two milliliters of drug dilution (10X) are added to sterile screw cap bottles to which 18 ml of Mueller-Hinton agar containing 5.6% defibrinated sheep blood is added. Final drug concentration ranges 256 $\mu$g/ml–0.015 $\mu$g/ml in agar containing 5% sheep blood.
3. A few isolated colonies of each test organism are inoculated into 5 ml trypticase soy broth or brain heart infusion broth. The cultures are shaken at 35° C. for 5 hours.
4. Each culture is diluted 1:50 ($10^{-1.7}$) in Mueller-Hinton broth and applied to agar plates using a Steers replicator. Control plates should be seeded last to ensure that viable organisms were present throughout the procedure. Inoculated agar plates are allowed to stand undisturbed until the inoculum spots are completely absorbed.
5. The plates are inverted and incubated at 35° C. for 18 hours with $CO_2$.
6. The minimum inhibitory concentration (MIC) is taken as the lowest concentration of antimicrobial agent at which complete inhibition occurs. A very fine, barely visible haze or a single colony is disregarded.

The results are as follows:

IN VITRO ACTIVITY OF LL-E19020 EPSILON AND LL-E19020 EPSILON₁
MINIMAL INHIBITORY CONCENTRATION (MCG/ML)

| ORGANISM | LL-E19020 EPSILON | EPSILON | EPSILON₁ |
|---|---|---|---|
| 1. Staphylococcus aureus NEMC 87-69 | >128 | — | — |
| 2. Staphylococcus aureus ROSE (MP) | >128 | 8 | 16 |
| 3. Staphylococcus aureus IVES 6-542 | >128 | — | — |
| 4. Staphylococcus aureus IVES 5-160 | >128 | 4 | 8 |
| 5. Staphylococcus aureus IVES 5-396 | >128 | 4 | 8 |
| 6. Staphylococcus aureus VGH 84-47 | >128 | 8 | 8 |
| 7. Staphylococcus aureus CMC 83-131 | >128 | 16 | 32 |
| 8. Staphylococcus aureus SMITH (MP) | >128 | 4 | 4 |
| 9. Staphylococcus aureus ATCC 25923 | >128 | 8 | 32 |
| 10. Staphylococcus aureus ATCC 29213 | >128 | 16 | 16 |
| 11. Staphylococcus haemolyticus AVAH 88-1 | >128 | 32 | 32 |
| 12. Staphylococcus haemolyticus AVAH 88-3 | >128 | 16 | 16 |
| 13. Staphlococcus k 82-26 | >128 | — | — |
| 14. Staphylococcus epidermidis IVES 455 | >128 | 4 | 8 |
| 15. Staphylococcus epidermidis ATCC 12228 | >128 | — | — |
| 16. Enterococcus spp. ARUM 87-41 | >128 | 32 | 64 |
| 17. Enterococcus spp. CHBM 88-60 | >128 | 64 | 64 |
| 18. Enterococcus spp. WRVA 88-33 | >128 | 64 | 128 |
| 19. Enterococcus spp. UCI 85-30 | >128 | 32 | 64 |
| 20. Enterococcus spp. VGH 84-69 | >128 | 32 | 64 |
| 21. Enterococcus spp. CMC 83-120 | >128 | 32 | 128 |
| 22. Streptococcus pyogenes AMCH 88-84 | 4 | .12 | .5 |
| 23. Streptococcus pyogenes AMCH 88-86 | 8 | .25 | .5 |
| 24. Streptococcus pyogenes C203 (MP) | — | 1 | 2 |
| 25. Streptococcus pneumoniae CHBM 88-70 | 8 | — | — |
| 26. Streptococcus pneumoniae CHBM 88-75 | 4 | — | — |
| 27. Streptococcus pneumoniae TEX 85-2 | 16 | .5 | 2 |
| 28. Bacillus cereus DAVIES | >128 | 64 | 128 |
| 29. Klebsiella pneumoniae NEMC 87-271 | >128 | >128 | >128 |
| 30. Escherichia coli ATCC 25922 | >128 | >128 | >128 |
| 31. Escherichia coli ATCC 35218 | >128 | >128 | >128 |
| 32. Escherichia coli D-21 | >128 | — | — |
| 33. Escherichia coli D-22 | >128 | — | — |
| 34. Pseudomonas aeruginosa 12-4-4 (MP) | — | >128 | >128 |

As can be seen from the in vitro data above, LL-E19020 Epsilon and LL-E19020 Epsilon₁ are antibacterial agents.

Antibiotics LL-E19020 Epsilon and LL-E19020 Epsilon₁ derive their utility from antibacterial activity. For example these antibiotics may be used in the suppression of bacterial infections, as a topical antibacterial agent and as a general disinfectant for laboratories.

In addition to their antibacterial activity these compounds are effective as anticoccidial agents in poultry and as growth promotant and anthelmintic agents. These utilities are the subject of patent application Ser. No. 07/756,938 filed concurrently herewith and incorporated herein by reference.

In therapeutic use, the compounds of this invention may be administered in the form of a conventional pharmaceutical composition appropriate for the intended use. Such a compositions may be formulated so as to be suitable for oral, parenteral, or topical administration. The active ingredient may be combined in admixture with a nontoxic pharmaceutically acceptable carrier, which carrier may take a wide variety of forms depending on the form of preparation desired for administration, i.e., oral, parenteral or topical.

When the compounds are employed for the above utility, they can be combined with one or more pharmaceutically acceptable carriers, for example. solvents, diluents and the like, and may be administered orally in such forms as tablets, capsules, dispersible powders, granules, or suspensions containing, for example, from about 0.05 to 5% of suspending agent, syrups containing, for example from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

An effective amount of compound from 0.2 mg/kg of body weight to 100.0 mg/kg of body weight should be administered one to five times per day via any topical route of administration including but not limited to oral, parenteral (including subcutaneous, intravenous, intramuscular, intrasternal injection or infusion techniques), by inhalation spray, or rectally, in dosage unit formulations containing conventional non-toxic pharmaceutically acceptable carriers, adjuvants and vehicles. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the stand-point of ease of preparation and administration are solid compositions, particularly tablets and hard-filled or liquid-filled capsules. Oral administration of the compound is preferred.

These active compounds may also be administered parenterally or intraperitoneally. Solutions or suspensions of these active compounds as a free base or pharmacologically acceptable salt can be prepared in water suitably mixed with a surfactant such as hydroxy propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oil.

We claim:

1. A compound LL-E19020 Epsilon comprising
(a) the structure

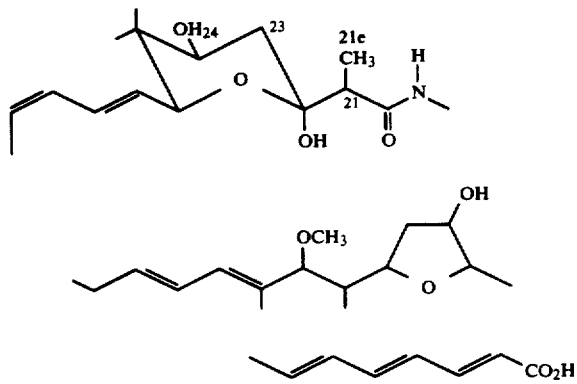

(b) a molecular weight of 643 (FABMS=M/Z 666 corresponding to [M+Na]+).
(c) a specific optical rotation:

$$[\alpha]_D = +24°(1.53, MeOH)^{26}$$

(d) a characteristic ultraviolet absorption spectrum as shown in FIG. I of the attached drawings;
(e) a characteristic infrared absorption spectrum as shown in FIG. II of the attached drawings;
(f) characteristic proton nuclear magnetic resonance spectrum as shown in FIG. III of the attached drawings;
(g) a characteristic carbon-13 nuclear magnetic resonance spectrum as shown in FIG. IV of the attached drawings;
(h) a characteristic HPLC retention time of 12.6 minutes using a gradient of acetonitrile in aqueous acetic acid; and
(i) a characteristic HPLC retention time of 11.4 minutes using a gradient of dioxane in aqueous acetic acid.

2. A compound LL-E19020 Epsilon$_1$ comprising
(a) the structure

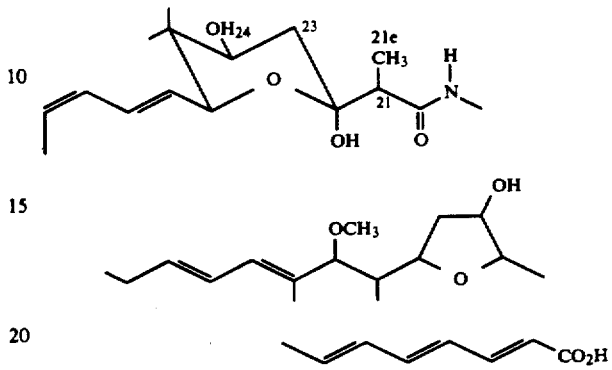

(b) a molecular weight of 643 (Thermospray ms=M/Z for m−).
(c) a characteristic ultraviolet absorption spectrum as shown in FIG. V of the attached drawings;
(d) a characteristic infrared absorption spectrum as shown in FIG. VI of the attached drawings;
(e) a characteristic proton nuclear magnetic resonance spectrum as shown in FIG. VII of the attached drawings;
(f) a characteristic carbon-13 nuclear magnetic resonance spectrum as shown in FIG. VIII of the attached drawings;
(g) a characteristic HPLC retention time of 9.9 minutes using a gradient of acetonitrile in aqueous acetic acid; and
(h) a characteristic HPLC retention time of 9.4 minutes using a gradient of dioxane in aqueous acetic acid.

3. An antibiotic pharmaceutical composition which comprises an antibiotic amount of LL-E19020 Epsilon$_1$ as defined in claim 2 in association with a pharmaceutically acceptable carrier.

4. Antibiotic pharmaceutical composition which comprises an antibiotic amount of LL-E19020 Epsilon as defined in claim 1 in association with a pharmaceutically acceptable carrier.

* * * * *